Figure 1:
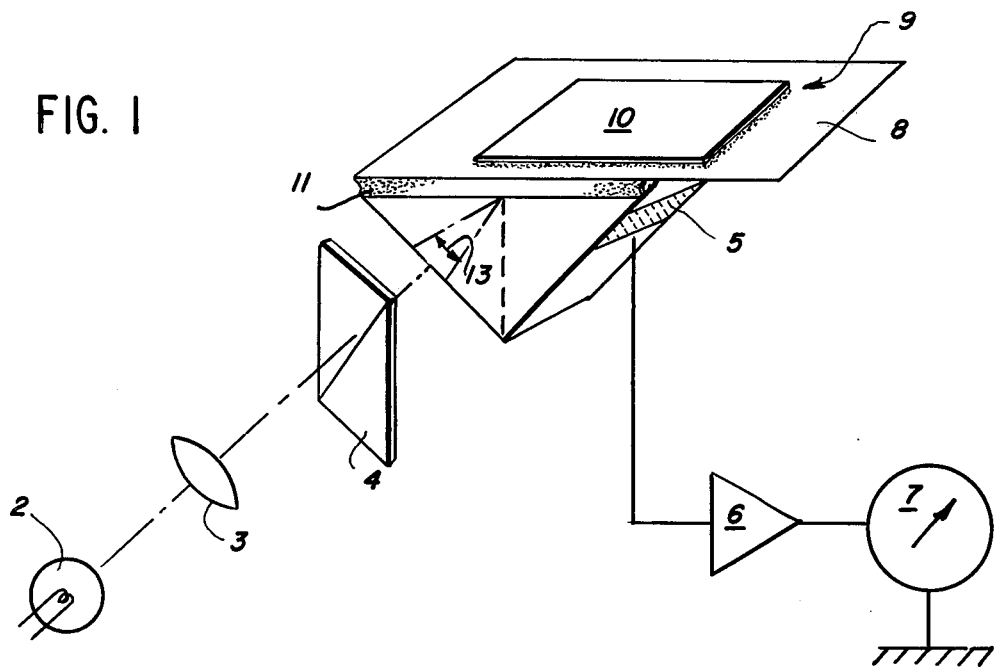

United States Patent [19]

Noller

[11] 4,181,441
[45] Jan. 1, 1980

[54] INTERNAL REFLECTANCE SPECTROMETER

[75] Inventor: Hans G. Noller, Glenview, Ill.

[73] Assignee: G. D. Searle & Co., Skokie, Ill.

[21] Appl. No.: 858,308

[22] Filed: Dec. 7, 1977

[51] Int. Cl.² .................. G01J 3/48; G01N 21/02
[52] U.S. Cl. ...................... 356/414; 250/573; 356/436
[58] Field of Search ............... 356/96, 201, 326, 436, 356/440, 414; 250/573, 574

[56] References Cited

U.S. PATENT DOCUMENTS

| 3,501,241 | 3/1970 | Hansen et al. | 356/244 |
| 3,939,350 | 2/1976 | Kronick et al. | 250/304 |
| 4,040,749 | 8/1977 | David et al. | 356/201 |

*Primary Examiner*—Vincent P. McGraw

*Attorney, Agent, or Firm*—Mary Jo Kanady; Roy A. Ekstrand; John J. McDonnell

[57] ABSTRACT

The present invention encompasses an internal reflectance spectrometer comprising:
(a) a prism adaptable for optically coupling test sample to one surface thereof;
(b) a means for irradiating the test sample with light of wave length absorbed by the test sample, said means directing light to enter the test sample from the prism surface having test sample thereon at an angle between the critical angle and about 35° less than the critical angle, said light refracted in the test samples so that said light is internally reflected from the test sample remote from the prism surface; and
(c) a means for detecting the internally reflected light.
The instrument of the present invention is a full range absorbtion spectrometer.

6 Claims, 2 Drawing Figures

U.S. Patent  Jan. 1, 1980  4,181,441

INTERNAL REFLECTANCE SPECTROMETER

The present invention encompasses an internal reflectance spectrometer comprising:

(a) a prism adaptable for optically coupling test sample to one surface thereof;

(b) a means for irradiating the test sample with light of wave length absorbed by the test sample, said means directing light to enter the test sample from the prism surface having test sample thereon at an angle between the critical angle and about 35° less than the critical angle, said light refracted in the test sample so that said light is internally reflected from the test sample remote from the prism surface; and (c) a means for detecting the internally reflected light.

The term prism adaptable for optically coupling test sample to one side refers to classical triangular glass or plastic prisms and optical equivalents thereof. Flint or crown glass prisms having 45° or 60° angles at the apex are suitable. One side of the prism is rotated for ease of access for application of test sample. The side of the prism to which the test sample is optically coupled is optionally fitted with side holders, sample cells, or other means for facilitating sampling.

Means for irradiating test sample refers to monochromatic light sources such as lasers as well as polychromatic light sources such as filament and vapor lamps in combination with filter or other monochromator to provide light of the wavelength absorbed by the test sample. Preferably the light is collimated to provide a parallel beam.

Photoelectric cells such as photoemissive alkali metal or oxide type (sodium, potassium, cesium) with which an external source of electromotive force must be employed and photovoltaic or barier-layer selenium or cuprous oxide cells which generate their own electromotive force, photomultiplier tubes, blometers, and photoconductive cells are used in conjunction with conventional amplifiers and calibrated electrical read out devices such as a direct reading voltmeter to provide suitable means for detecting internally reflected light.

Test sample is optically coupled to one side of the prism by direct application or alternatively an immersion fluid film is applied directly to the surface of the prism and a glass slide is placed over the film. The test sample then is applied to the sample holding slide and a covering slide is added in order to obtain uniform thickness of the test sample film. For whole blood test samples, the sample holding slide is coated on one side with a sample absorbing material which separates red blood corpu from serum. The red blood corpuscles are washed away and measurements made as usual.

Thus, a collimated monochromated beam of light of wave length absorbed by the test sample enters one side of a prism so that it impinges upon a second side of the prism having test sample optically coupled thereto at an angle less than the critical angle for total reflectance from the prism surface so that the light passes into test sample and is refracted in the test sample so that the light is internally reflected from the surface of the test sample remote from the surface of the second side of the prism and exits the prism through a third side falling upon a means for detecting the internally reflected light. Therefore, in context of the triangular prism one side of the prism has test sample optically coupled thereto, the means for irradiating the test sample is aligned opposite a second side of the prism so that light enters the test sample at an angle between the critical angle and about 35° less than the critical angle, and the means for detecting internally reflected light is located opposite a third side of the prism. Most typically the means for irradiating is aligned so that light enters the test sample or immersion fluid at an angle between the critical angle and 45°.

FIG. 1, Schematic diagram of the internal reflectance spectrometer.

Figure 2:
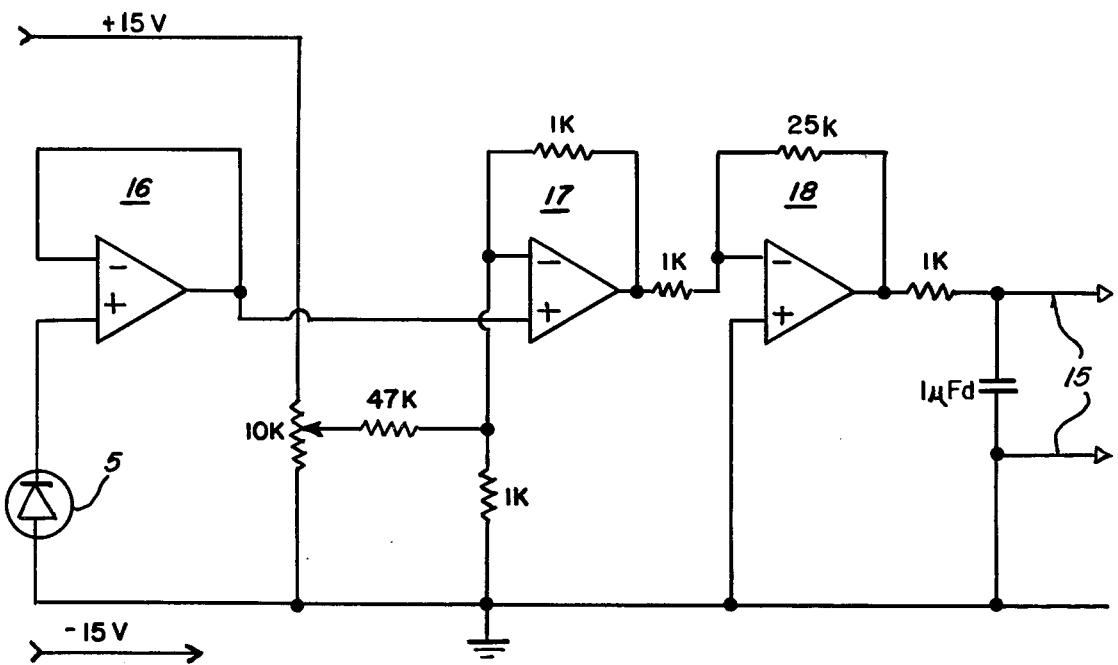

FIG. 2, Operational amplifier circuit.

Referring to FIG. 1, light from light source 2 is collimated by a lens collimator 3 and passes through interference filter 4 to provide a beam of collimated light of wave length absorbed by the test sample. This beam of light is directed through one side of the prism 1 at an angle between critical angle and about 35° less than the critical angle 13. The light passes into an immersion fluid film 11 through the sample holding slide 8 and into the test sample 9. The light is then internally reflected to the photocell 5 and the resulting voltage is multiplied by an operational amplifier 6 and then to read-out system 7. Optionally, the test sample 9 is in direct contact with the prism surface and 8 and 11 are not needed. It is generally desirable to use a coverglass 10 whether test sample 9 is directly or indirectly coupled to the prism 1 surface.

FIG. 2 represents a schematic diagram of an operational amplifier for multiplying the voltage produced by the photocell. 5 Designates the photocell, 15 designates the leads to a DVM (direct reading voltmeter), as a readout shown as 7 in FIG. 1, 16 is a unity gain circuit which prevents the amplifier from loading the photocell, 17 represents an operational amplifier circuit for biasing and zeroing the output, and 18 is the amplifier portion of the circuit. K is kiloohm resistor, V is voltage, μfd is microfared capacitor. Critical angle, $i_c$, 13, FIG. 1, is the angle formed between the interphase of two media and a beam of light; beyond the critical angle light is internally reflected, below the $i_c$, closer to the perpendicular, the light penetrates the optical coupling system or directly into the test sample if optical coupling is not used. The critical angle is determined by $\sin^{-1} i_c = N_2/N_1$ where $N_1$ is the refractive index of the prism and $N_2$ is the refractive index ot test sample in a system where the sample is directly placed on the prism surface.

TABLE 1

|  | $N_2$ | $N_1$ |
|---|---|---|
| Water | 1.344 | Crown glass 1.52 |
| Bilirubin Std. | 1.34 | Flint glass 1.58 |
| Plasma | 1.33–1.36 |  |

|  | $N_1$ | $N_1$ |
|---|---|---|
|  | 1.52 | 1.58 |
| $i_c$ ($N_2$ = 1.34) | 61.83° | 58.04° |
| $i_c$ ($N_2$ = 1.333) | 61.28° | 57.53° |
| $i_c$ ($N_2$ = 1.344) | 62.15° | 58.28° |

Table 1 Critical angles calculated for typical applications in clinical chemistry.

$$i_c = \sin^{-1} N_2 N_1$$

Internal reflectance spectroscopy is extensively discussed in the prior art. Wilks "A Practical Approach to Internal Reflection Spectroscopy" November 1972, page 42–55, discusses principles and applications of Internal Reflection Spectroscopy. Harrich and Loeb, Analytical Chemistry, Vol. 45, No. 4, April 1973, pp 687, discusses Multiple Internal Reflection Fluorescence Spectrometry, and Report from Department of Electrical Engineering College of Engineering University of Washington, Seattle, Washington 98195 (NIA Grant GM 16436), discusses the application of a laser attenuated reflectance device for measuring bilirubin. These devices operate at greater than the critical angle $i_c$ so that the light is reflected in the prism and only very slightly penetrates into the test sample. The main problem with this approach is that penetration is slight and has required the development of multibounce techniques in order to achieve sufficient sensitivity [see N.J. Harrick American Laboratory 63 (1973) and NIH Grant GM 16436].

The present invention overcomes this prior art difficulty by setting the internal reflectance conditions at the surface of the test sample remote from the prism and thereby provides a single bounce technique whereby the light transverses the test sample film about 2 times and thus provides for greater sensitivity and obviates the need for a multibounce system.

In a preferred embodiment a 60° Crown glass prism having a refractive index of 1.52 is used in combination with a lens collimater and a filter transmitting light of about 455–470 nm and a selenium photocell to measure bilirubin in a serum sample in concentration from 0–30 mg/%. The serum sample is placed on an untreated Crown glass sample holding slide which is optically coupled to the prism with 1.651 refractive index coupling oil. The incident angle is set as less than 60°. The determination of concentration is made by a standard concentration versus millivolt reading curve from which an unknown can be determined or alternately a direct mg/% read-out can be used for an instrument that functions as a bilirubinometer. Those skilled in analytical chemical arts will recognize the usefulness of the present invention for other clinical applications as well as colorimetric analysis in general.

Sample holding slides coated on one side with sample absorbing material which does not interfere with transmission of light of wave length to be absorbed are particularly useful for measurement of constituents of whole blood without interference from red blood corpuscles. Thus the blood serum is absorbed into the sample absorbing material and the blood corpuscles remain on top of the layer and do not interfere with the measurement. As usual the side of the sample holding slide not coated is optically coupled to the prism with immersion fluid.

In a preferred embodiment the sample holding slide made of glass is uniformly coated on one side with gelatin, as sample absorbing material. Whole blood is applied to the gelatin layer and the serum is allowed to absorb into the gelatin. The red blood corpuscles are rinsed away and the uncoated side of the sample holding slide is optically coupled to prism and bilirubin content of the serum is measured by irradiation with light of 455–470 nm at a angle between the critical angle and 35° less than the critical angle and measuring the internally reflected light. 0–30 mg-percent bilirubin in 20–50 µl blood sample are conveniently measured by this technique.

This invention has been described with particular reference to the drawings. However, they are not meant to limit the invention either in spirit or in scope as many variations and modifications will be apparent to those skilled in the art.

What is claimed is:

1. an internal reflectance spectrometer comprising:
   (a) a prism adaptable for optically coupling a test sample to one surface thereof; forming a sample-prism boundary
   (b) a means for irradiating the test sample with light of wave length absorbed by the test sample, said means directing light to enter the test sample from the prism surface having said test sample thereon such that said light forms an angle with said boundary between the critical angle and about 35 less that the critical angle, said light being refracted in the test sample so that said light is internally reflected from the test sample remote from said boundary; and
   (c) a means for detecting internally reflected light.

2. An internal reflectance spectrometer according to claim 1, wherein the test sample is in direct contact with the prism.

3. An internal reflectance spectrometer according to claim 1 wherein the test sample is optically coupled to the prism through an immersion fluid and sample holding slide.

4. An internal reflectance spectrometer according to claim 1 wherein the means for detecting internally reflected light is a photocell in combination with an operational amplifier and calibrated electrical read-out device.

5. An internal reflectance spectrometer according to claim 1 wherein light of about 455–470 nm is used to irradiate a test sample containing bilirubin.

6. An internal reflectance spectrometer, according to claim 1, wherein a sample holding slide coated with sample absorbing material on one side is optically coupled to the prism.

* * * * *